(12) United States Patent
Chang (10) Patent No.: US 9,743,882 B2
(45) Date of Patent: Aug. 29, 2017

(54) SYSTEMS, APPARATUS, AND METHODS FOR DOCUMENTING CODE BLUE SCENARIOS

(71) Applicant: LOS ANGELES BIOMEDICAL RESEARCH INSTITUTE AT HARBOR-UCLA MEDICAL CENTER, Torrance, CA (US)

(72) Inventor: Ruey-Kang Chang, Diamond Bar, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 309 days.

(21) Appl. No.: 14/245,858

(22) Filed: Apr. 4, 2014

(65) Prior Publication Data
US 2015/0282758 A1    Oct. 8, 2015

(51) Int. Cl.
| | |
|---|---|
| A61B 5/00 | (2006.01) |
| A61M 16/04 | (2006.01) |
| A61N 1/39 | (2006.01) |
| A61B 5/113 | (2006.01) |
| A61B 5/0205 | (2006.01) |
| A61H 31/00 | (2006.01) |
| A61B 5/01 | (2006.01) |
| A61B 5/021 | (2006.01) |
| A61B 5/024 | (2006.01) |
| A61B 5/08 | (2006.01) |

(52) U.S. Cl.
CPC ........ *A61B 5/4848* (2013.01); *A61B 5/02055* (2013.01); *A61B 5/6823* (2013.01); *A61B 5/6833* (2013.01); *A61H 31/005* (2013.01); *A61B 5/01* (2013.01); *A61B 5/021* (2013.01); *A61B 5/024* (2013.01); *A61B 5/08* (2013.01); *A61B 5/113* (2013.01); *A61B 2560/0214* (2013.01); *A61B 2560/0242* (2013.01); *A61B 2560/0412* (2013.01); *A61B 2560/0475* (2013.01); *A61B 2560/0493* (2013.01); *A61H 2201/501* (2013.01); *A61H 2201/5043* (2013.01); *A61H 2201/5048* (2013.01);
(Continued)

(58) Field of Classification Search
CPC ............ A61H 2230/00; A61H 2230/06; A61H 2230/207; A61H 2230/30; A61H 2230/50; A61H 2230/65; A61B 5/4848; A61B 5/6823
See application file for complete search history.

(56) References Cited

U.S. PATENT DOCUMENTS

| | | | |
|---|---|---|---|
| 2005/0055242 A1 | 3/2005 | Bello et al. | |
| 2005/0251214 A1* | 11/2005 | Parascandola | G09B 23/288 607/5 |

(Continued)

*Primary Examiner* — William Thomson
*Assistant Examiner* — Amanda Steinberg
(74) *Attorney, Agent, or Firm* — Pillsbury Winthrop Shaw Pittman LLP (57) ABSTRACT

An apparatus may be configured for documenting a code blue scenario when adhered to the chest of a subject undergoing resuscitation by sensing and transmitting information associated with the code blue scenario. Such information may include one or more of vital signs of the subject during resuscitation, information associated with chest movements of the subject during resuscitation, and audio information from an environment of the subject during resuscitation. A computing platform that is separate and distinct from the apparatus may provide code blue documentation conveying information related to the vital signs of the subject and derived from the audio information from the environment of the subject during resuscitation.

25 Claims, 6 Drawing Sheets

(52) U.S. Cl.
CPC ............ *A61H 2201/5058* (2013.01); *A61H 2201/5084* (2013.01); *A61H 2201/5097* (2013.01); *A61H 2230/00* (2013.01); *A61H 2230/06* (2013.01); *A61H 2230/207* (2013.01); *A61H 2230/30* (2013.01); *A61H 2230/50* (2013.01); *A61H 2230/65* (2013.01); *A61M 16/04* (2013.01); *A61M 2205/3553* (2013.01); *A61M 2205/3584* (2013.01); *A61M 2205/502* (2013.01); *A61M 2205/581* (2013.01); *A61M 2230/04* (2013.01); *A61M 2230/205* (2013.01); *A61M 2230/30* (2013.01); *A61M 2230/42* (2013.01); *A61M 2230/50* (2013.01); *A61N 1/3937* (2013.01)

(56) References Cited

U.S. PATENT DOCUMENTS

| | | | |
|---|---|---|---|
| 2005/0277872 A1* | 12/2005 | Colby, Jr. | A61B 5/0022 604/67 |
| 2006/0223042 A1* | 10/2006 | Epler | G09B 7/00 434/323 |
| 2008/0089313 A1 | 4/2008 | Cayo et al. | |
| 2008/0312519 A1 | 12/2008 | Maschke | |
| 2008/0312565 A1 | 12/2008 | Celik-Butler et al. | |
| 2009/0055735 A1* | 2/2009 | Zaleski | G06F 19/3406 715/700 |
| 2009/0143045 A1* | 6/2009 | Graves | A61B 5/02055 455/404.1 |
| 2010/0114218 A1 | 5/2010 | Heath et al. | |
| 2011/0237924 A1* | 9/2011 | McGusty | A61B 5/0006 600/391 |
| 2012/0083720 A1 | 4/2012 | Centen et al. | |
| 2012/0123224 A1* | 5/2012 | Packer | G06F 19/327 600/301 |
| 2012/0136404 A1* | 5/2012 | Drew | A61N 1/3993 607/6 |
| 2012/0150058 A1 | 6/2012 | Zubrow | |
| 2012/0197324 A1* | 8/2012 | Nova | A61N 1/3931 607/4 |
| 2012/0306662 A1* | 12/2012 | Vosch | H04Q 9/00 340/870.07 |
| 2012/0323591 A1 | 12/2012 | Bechtel et al. | |
| 2013/0046543 A1 | 2/2013 | Kitchens et al. | |
| 2013/0120140 A1 | 5/2013 | Patil et al. | |

* cited by examiner

SYSTEMS, APPARATUS, AND METHODS FOR DOCUMENTING CODE BLUE SCENARIOS

FIELD OF THE DISCLOSURE

This disclosure relates to systems, apparatus, and methods for documenting a code blue scenario in which a subject is undergoing resuscitation.

BACKGROUND

Patient safety is one of the most important challenges facing today's healthcare. There are approximately 2.5 million deaths in the U.S. each year, about a third of which occur in acute care hospitals. Unless there are "do-not-resuscitate" advanced directives in place, patients who die in a hospital most likely have undergone one or more resuscitation attempts known as "code blue." Code blue is used by hospitals to describe a scenario in which a patient with cardiac or respiratory arrest requires stat medical intervention (i.e., resuscitation). Medical errors occur in healthcare every day. In code blue scenarios, medical errors may be likely to occur, which can cost lives. Common errors in cardiopulmonary resuscitation (CPR) may include slow chest compression rates, shallow chest compression depths, hyperventilation, long pauses in CPR before shock delivery, delivery of electrical defibrillation for nonshockable rhythms, medication errors, failure to follow resuscitation guidelines (e.g., advanced cardiovascular life support (ACLS), pediatric advanced life support (PALS), and/or other guidelines), and/or other errors.

Studies have found conventional paper-based documentation practices of code blue scenarios may be inaccurate, often misreporting intervention delivery times, missing their delivery entirely, and/or making other documentation errors. Paper-based code blue records may commonly have missing time data, include use of multiple timepieces for recording time data during the same event, and convey a wide variation in coherence and precision of clocking devices. For example, the documentation of time in emergency events has been shown to vary significantly, by as much as nineteen minutes, depending on which clocking devices are used. Furthermore, incomplete and inaccurate documentation of code blue scenarios are frequently a source for medicolegal disputes.

SUMMARY

Exemplary implementations may provide complete and accurate documentation of code blue scenarios, which may facilitate quality improvement of resuscitation in practice, enhance in patent safety, and protect healthcare professionals against lawsuits. Some implementations provide an electronic apparatus for complete documentation of code blue scenarios. This apparatus may be referred to as a "BlueBox." According to one implementation, the apparatus may include a five by ten centimeter elongated patch configured to be placed next to the mid-sternum on the left. Other configurations are contemplated. The apparatus may be configured to provide complete capture of all code blue events including vital signs of a subject (e.g., a patient or other individual undergoing resuscitation), cardiac rhythm, verbal orders, execution of the orders, chest compression, cardioversion/defibrillation, procedures, medications, labs, and/or other events. The apparatus may enhance the safety of subjects undergoing CPR. The apparatus may provide electronic code blue records that can be useful for electronic medical record (EMR) documentation, education, and quality improvement.

The apparatus may include multiple sensors embedded in a micro-electronics platform. The sensors may include electrocardiogram (ECG) sensors, one or more accelerometers (e.g., a tri-axial accelerometer), a temperature sensor, an impendence sensor, one or more acoustic sensors, one or more sensors configured for detecting oxygen saturation ($SpO_2$) (e.g., pulse oximeter sensors), and/or other sensors. In some implementations, all of the sensors may be integrated into a volume with a four centimeter diameter and eight millimeter thickness. Vital signs and audio information may be simultaneously recorded with corresponding time stamps. Security measures may be implemented to protect the recorded information. An enclosure and contact surface of the apparatus may be designed to withstand pressure from chest compressions and/or voltages from cardioversion and defibrillation.

An "electronic code blue sheet" user interface may be provided to display the code blue events recorded by the apparatus. In accordance with some implementations, the user interface may be provided by an app suitable for one or more platforms including Apple iOS™ platform, Android™ platform, Microsoft Windows™, and/or other platforms. The app may retrieve information recorded by the apparatus via a wireless connection, and automatically display the code blue events chronologically with time stamps, in some implementations. The user interface may provide zoomable views of the vital signs. The user interface may facilitate playback of the audio information. In some implementations, a trained transcriptionist may annotate additional events, such as procedures and medications, based on the voice recordings. This annotation may be performed automatically with the aid of voice recognition technology, in some implementations. The electronic code blue sheet may be exported (e.g., as a portable document file (PDF) and/or other electronic document formats) so that the code blue sheet can be printed for paper medical record, or for uploading to EMR.

One aspect of the disclosure relates to an apparatus configured for documenting a code blue scenario when adhered to the chest of a subject undergoing resuscitation. The apparatus may comprise an enclosure and a sensor bank. The enclosure may be configured to withstand compressive forces applied to the subject's chest during resuscitation of the subject such that components disposed within the enclosure are protected from mechanical damage. The sensor bank may be at least partially disposed within the enclosure. The sensor bank may be configured to provide signals conveying information associated with a code blue scenario. The information may include vital signs of the subject during resuscitation and audio information from an environment surrounding the subject during resuscitation.

Another aspect of the disclosure relates to a system configured for documenting code blue scenarios. The system may comprise one or more physical processors configured to receive information from an apparatus configured for documenting a code blue scenario when adhered to the chest of a subject undergoing resuscitation by sensing and transmitting information associated with the code blue scenario. The information may include vital signs of the subject during resuscitation and audio information from an environment of the subject during resuscitation. The one or more physical processors may be disposed at a location other than the apparatus. The one or more processors may be further configured to execute computer program instructions. The computer program instructions may comprise a code blue documentation component configured to provide code blue documentation that conveys information related to the vital signs of the subject during resuscitation and the audio information from the environment of the subject during resuscitation.

Yet another aspect of the disclosure relates to a method for documenting code blue scenarios. The method may comprise receiving, using one or more physical processors, vital sign information associated with vital signs of a subject during resuscitation in a code blue scenario. The vital sign information may be received from an apparatus configured to be adhered to the chest of the subject when the code blue scenario begins. The method may comprise receiving, using one or more physical processors, audio information from an environment surrounding the subject during resuscitation. The audio information may be received from the apparatus. The method may comprise providing, using one or more physical processors, code blue documentation that conveys information related to the resuscitation performed on the subject. The code blue documentation may be based on both the vital sign information and the audio information.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
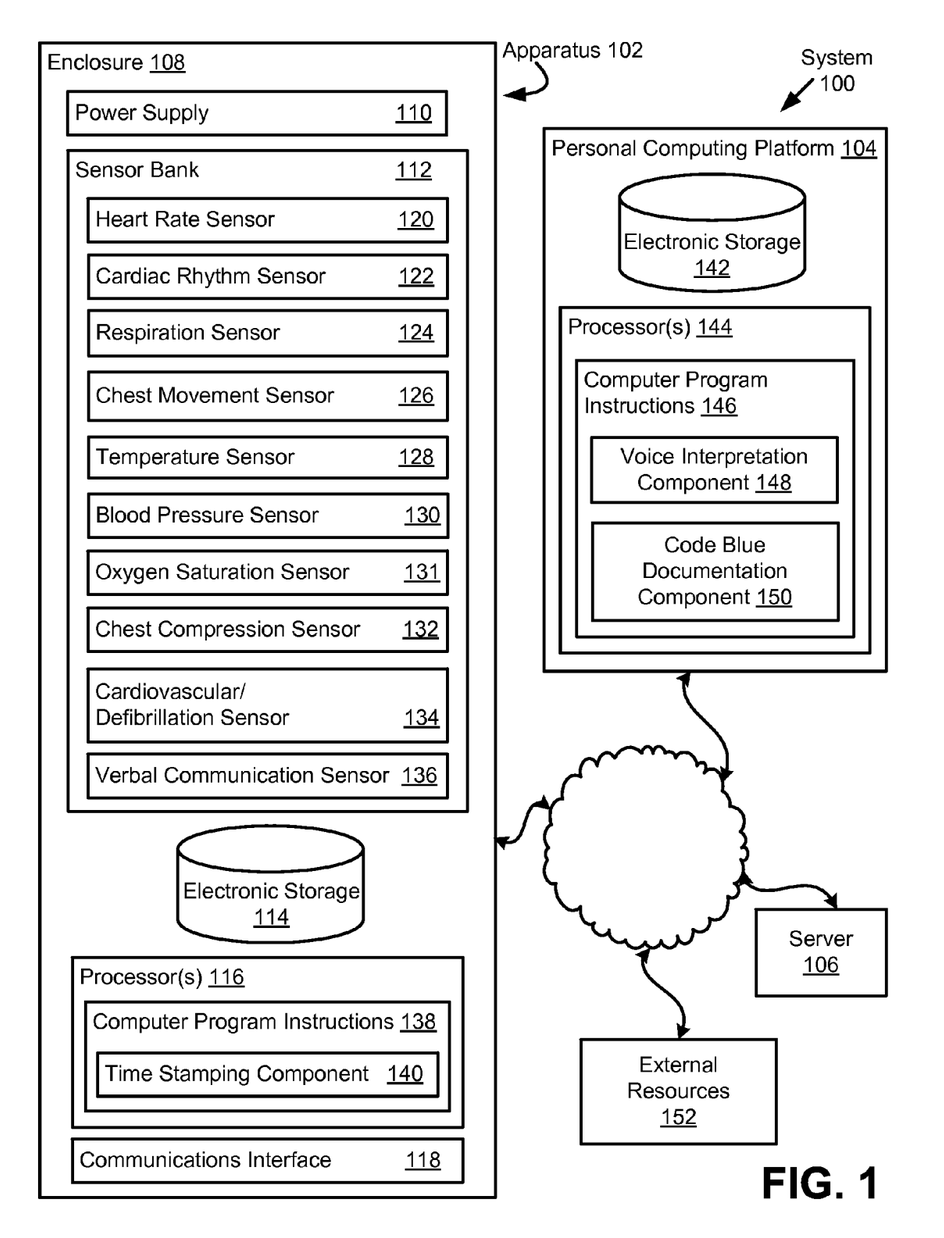
FIG. 1 illustrates a system configured for documenting code blue scenarios, in accordance with one or more implementations.

FIG. 1 illustrates a system 100 configured for documenting code blue scenarios, in accordance with one or more implementations. The system 100 may provide complete documentation for code blue scenarios, which may be useful for EMR integration, medical education, quality improvement, medicolegal purposes, and/or other purposes. The system 100 may provide standardized code blue documentation that is complete and operator-independent, thus improving quality of care and protecting patient safety. According to some implementations, system 100, with its capacity to capture most or all events in code blue scenarios, may provide much needed assurance to healthcare professionals who lead code blue teams (e.g., anesthesiologists, intensivists, emergency physicians, and/or other healthcare professionals).

Components of system 100 may continuously record important vital parameters of a subject undergoing CPR, procedures such as chest compression and defibrillation, and all verbal communications among the code blue team members such as orders, responses, medications, lab results, and/or other verbal communications. Proper documentation of code blue scenarios may facilitate detailed reviews of CPR events for quality improvement, thus enhancing patent safety. Proper documentation may protect healthcare professionals against lawsuits which might otherwise be due to incomplete or inaccurate documentation. Properly documenting care in a patient's medical records is essential and, in the event of a lawsuit, provides evidence that the care that was provided met professional standards. If there is no documentation, there's no evidence.

In one exemplary implementation, system 100 may include an apparatus shaped as a disk having a diameter of four centimeter diameters and a thickness of one centimeter, housed in a ten by five centimeter patch shaped as a big Band-Aid. The apparatus may be configured to be placed on the left mid chest, over the fourth intercostal space between the left sternal border and left nipple, at the beginning of a code blue scenario. There may be no control buttons or other mechanisms on the apparatus. Instead, the apparatus may power on and begin recording responsive to a protective cover being removed. This may be achieved using a magnetic switch, according to some implementations. The apparatus may power off and stop recording responsive to the apparatus being removed from the subject. The apparatus may be configured to prevent unauthorized removal of any internal memory and/or tampering with recorded information.

Figure 2:
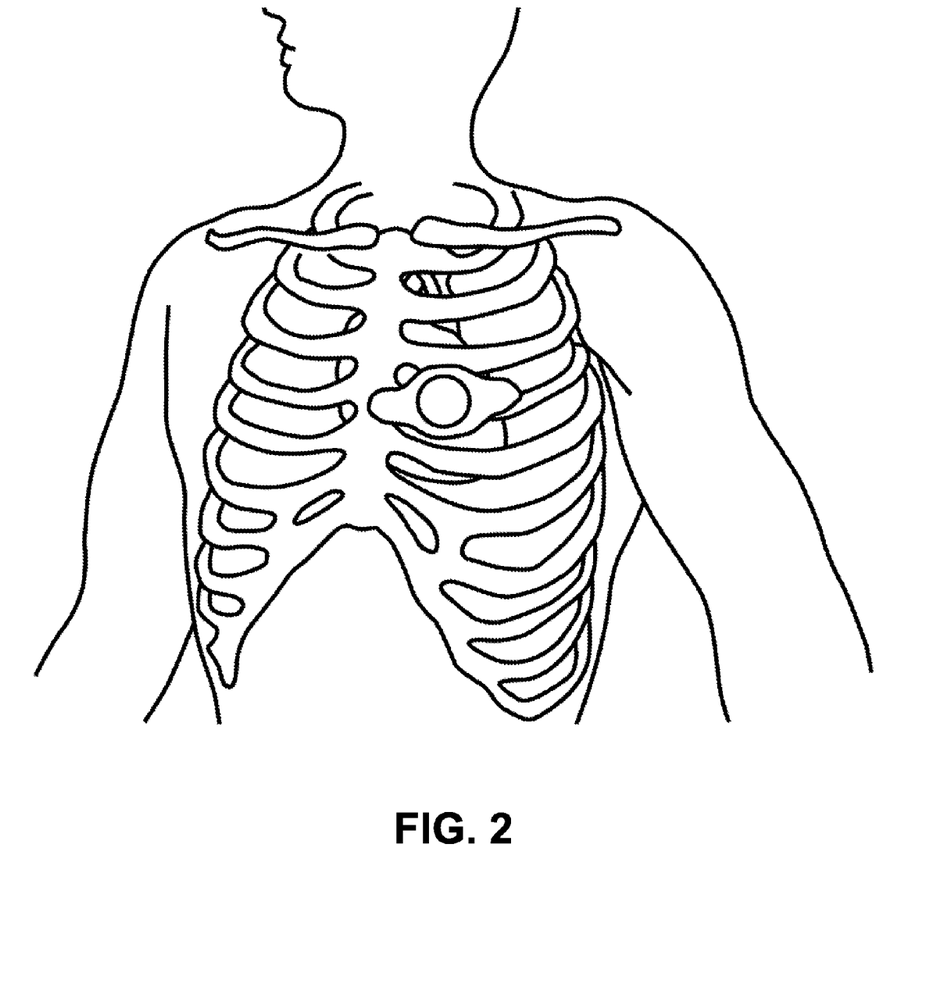
FIG. 2 illustrates an exemplary positioning of an apparatus configured for documenting a code blue scenario when adhered to the chest of a subject undergoing resuscitation, in accordance with one or more implementations.

As depicted in FIG. 1, system 100 may include an apparatus 102, a personal computing platform 104, a server 106, and/or other components. The apparatus 102 may be configured for documenting a code blue scenario when adhered to the chest of a subject undergoing resuscitation. FIG. 2 illustrates an exemplary positioning of an apparatus that is the same or similar to apparatus 102, in accordance with one or more implementations. The position of apparatus 102 depicted in FIG. 2 is not intended to be limiting as other positions are contemplated and are within the scope of the disclosure. For example, in some implementations, the position may be at a different location of the subject or covering a different shape or size area on the subject than that depicted in FIG. 2.

Referring again to FIG. 1, apparatus 102 may include an enclosure 108. The enclosure 108 may be configured to withstand compressive forces applied to the subject during resuscitation such that components disposed within enclosure 108 are protected from mechanical damage (e.g., breaking or otherwise becoming unable to operate properly due to receipt of compressive forces). The enclosure 108 may be configured to withstand electrical conditions (e.g., high voltages) resulting from defibrillation being performed on the subject such that component disposed within enclosure 108 are protected from electrical and/or magnetic damage (e.g., shorting or otherwise becoming unable to operate properly due to exposure to certain electrical conditions).

The enclosure 108 may have an adhesive applied to an external portion of enclosure 108 to facilitate removably adhering to the subject's chest. The apparatus 102 may be prepared with a removable cover or film (not depicted) that protects the adhesive on enclosure 108, and exposes the adhesive when removed.

Figure 3:
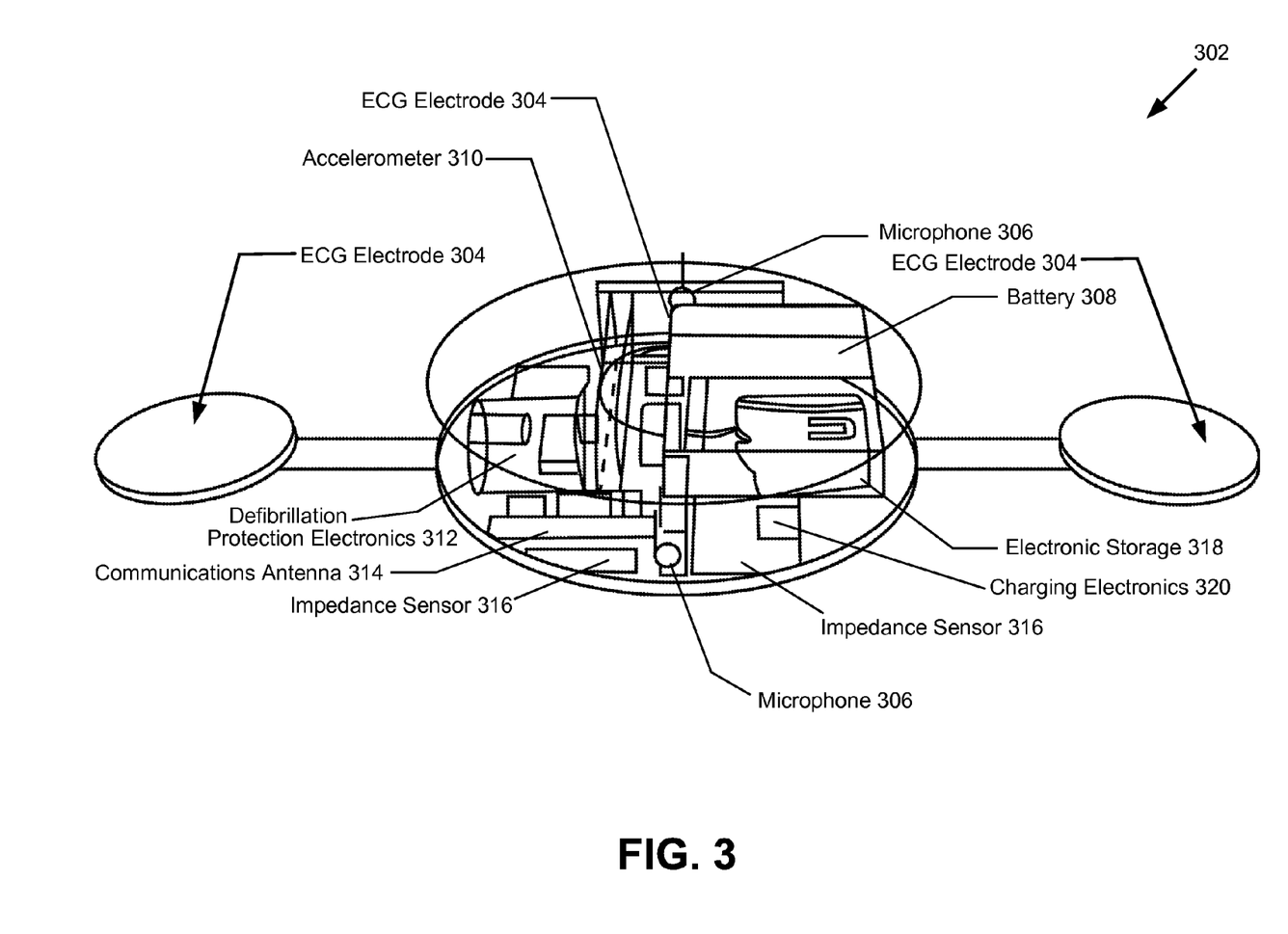
FIG. 3 illustrates an electronics hardware footprint and configuration of the apparatus, in accordance with one or more implementations.

FIG. 3 illustrates an electronics hardware footprint and configuration 302 of apparatus 102, in accordance with one or more implementations. The electronics hardware footprint and configuration 302 may include are area in which one or more components of apparatus 102 are disposed. As depicted in FIG. 3, electronics hardware footprint and configuration 302 may include one or more of ECG electrodes 304, microphones 306, a battery 308, an accelerometer 310, defibrillation protection electronics 312, communications antenna 314, impedance sensors 316, electronic storage 318, charging electronics 320, and/or other components. In some implementations, there may be no physical buttons, physical switches, or plug-style ports associated with electronics hardware footprint and configuration 302. In some implementations, electronics hardware footprint and configuration 302 may include one or more indicator lights (not depicted) configured to convey a status of apparatus 100 (e.g., recording, not recording, and/or other statuses).

Other configurations for electronics hardware footprint and configuration 302 are contemplated. The positions of various components on electronics hardware footprint and configuration 302 may vary according to different implementations. The shape and/or size of electronics hard ware footprint and configuration 302 depicted in FIG. 3 are not intended to be limiting as other shapes and/or sizes are contemplated and are within the scope of the disclosure. For example, in some implementations, the shape of electronics hardware footprint and configuration 302 may be more complex (e.g., more constituent shapes, curves, or angles) or less complex (e.g., less constituent shapes, curves, or angles) than that depicted in FIG. 3. In addition, there may be more or less sensor positions at the same or different locations on electronics hardware footprint 302. The size of electronics hardware footprint and configuration 302 may vary according to various factors includes a subject size (e.g., adult versus child), sensors sizes, and/or other factors.

Figure 4:
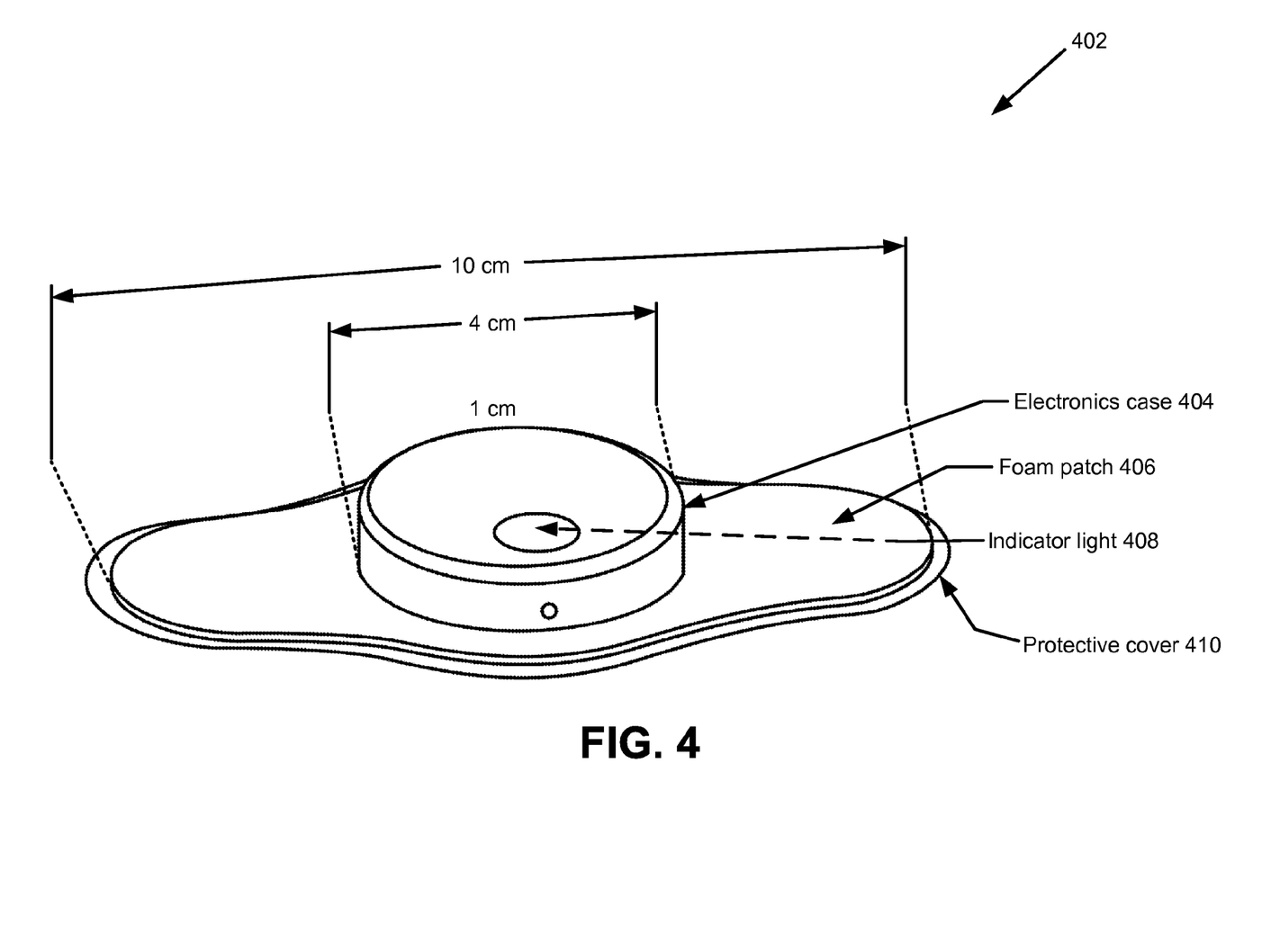
FIG. 4 illustrates an exemplary enclosure of the apparatus, in accordance with one or more implementations.

FIG. 4 illustrates an exemplary enclosure 402 of apparatus 102, in accordance with one or more implementations. The enclosure 402 may be similar to or the same as enclosure 108 described in connection with FIG. 1. The enclosure 402 may be configured to enclose some or all of electronics hardware footprint and configuration 302 (see FIG. 3). As depicted in FIG. 4, enclosure 402 may include one or more of an electronics case 404, a foam patch 406, an indicator light 408, a removable protective cover 410, and/or other components. The enclosure 108 may be made in whole or in part of one or more of acrylic, foam, plastic, metal, resin, and/or other materials. Pressure used for chest compressions may be up to 125 pounds. As such, enclosure 402 may be configured to withstand twenty or more pounds per square inch (PSI), or about 150 or more pounds of total force, according to some implementations. The enclosure 402 may include a hydrogel at a surface configured to contact skin on the subject. Such hydrogel may facilitate measurements by one or more of ECG sensors, temperature sensors, and/or other sensors. A surface of enclosure 402 may be configured to be adhered to skin of the subject. The removable protective cover 410 may cover an adhesive that facilitates adhesion by enclosure 402 to the subject. In some implementations, a magnetic switch (not depicted) may be included in enclosure 402 and be configured such that, responsive to a user removing the disposable cover and/or placing apparatus 102 on the subject, apparatus 102 may be powered on and/or collecting information associated with a code blue scenario.

Other configurations for enclosure 402 are contemplated. The shape and/or size of enclosure 402 depicted in FIG. 4 are not intended to be limiting as other shapes and/or sizes are contemplated and are within the scope of the disclosure. For example, in some implementations, the shape of enclosure 402 may be more complex (e.g., more constituent shapes, curves, or angles) or less complex (e.g., less constituent shapes, curves, or angles) than that depicted in FIG. 4. The size of enclosure 402 may vary according to various factors includes a subject size (e.g., adult versus child), sensors sizes, and/or other factors.

Referring again to FIG. 1, apparatus 102 may include one or more of a power supply 110, a sensor bank 112, electronic storage 114, one or more processors 116, a communications interface 118, and/or other components.

The power supply 110 may be disposed within enclosure 108. The power supply 110 may be configured to provide electrical power to one or more components of apparatus 102. The power supply 110 may be configured to provide electrical power to one or more components of apparatus 100 responsive to one or both of apparatus 100 being removably adhered to a subject's chest or an adhesive cover being removed from enclosure 108. The power supply 110 may include one or more of a battery, a capacitor, and/or other power supplies. The power supply 110 may be replaceable. According to various implementations, power supply 110 may be rechargeable using a conductive wire line in or an inductive wireless mechanism.

The sensor bank 112 may be at least partially disposed within enclosure 108. The sensor bank 112 may be configured to provide signals conveying information associated with a code blue scenario. The information may include vital signs of the subject during resuscitation and/or audio information from an environment surrounding the subject during resuscitation. The audio information from the environment may include voice commands issued during resuscitation of the subject. The audio information from the environment may include a vocal indication of a vital sign (e.g., blood pressure) of the subject during resuscitation.

In some implementations, sensor bank 112 may include one or more of a heart rate sensor 120, a cardiac rhythm sensor 122, a respiration sensor 124, a chest movement sensor 126, a temperature sensor 128, a blood pressure sensor 130, an oxygen saturation ($SpO_2$) sensor 131, a chest compression sensor 132, a cardioversion and/or defibrillation sensor 134, a verbal communication sensor 136, and/or other components.

The heart rate sensor 120 may be configured to provide a signal conveying information associated with a heart rate of the subject during resuscitation. By way of non-limiting example, the signal from heart rate sensor 120 may facilitate determining and/or presenting a heart rate of the subject, indications of when the subject's heart beats, and/or other information associated with the subjects heart function. In some implementations, heart rate sensor 120 may include one or more ECG sensors.

The cardiac rhythm sensor 122 may be configured to provide a signal conveying information associated with a cardiac rhythm of the subject during resuscitation. By way of non-limiting example, the signal from the cardiac rhythm sensor 122 may facilitate determining and/or presenting the subject's cardiac rhythm as shown by ECG, various types of arrhythmias (e.g., ventricular fibrillation), and/or other information associated with the subject's cardiac rhythm. In some implementations, cardiac rhythm sensor 122 may include one or more ECG sensors.

The respiration sensor 124 may be configured to provide a signal conveying information associated with a respiration of the subject during resuscitation. By way of non-limiting example, the signal from respiration sensor 124 may facilitate determining and/or presenting the subject's respiration rate, the subject's respiration volume, an indication of when the subject breaths, an indication of when a positive pressure ventilation was performed on the subject, an indication of how many positive pressure ventilations have been performed on the subject, an indication of a volume associated with positive pressure ventilations, and/or other information associated with the subject's breathing. In some implementations, respiration sensor 124 may include an impedance sensor.

The chest movement sensor 126 may be configured to provide a signal conveying information associated with chest movements caused by artificial respiration provided to the subject during resuscitation. By way of non-limiting example, the signal from chest movement sensor 126 may facilitate determining and/or presenting an indication of when an artificial breath was provided to the subject, and/or other information associated with artificial respiration provided to the subject. In some implementations, chest movement sensor 126 may include one or more accelerometers.

The temperature sensor 128 may be configured to provide a signal conveying information associated with a temperature of the subject during resuscitation. By way of non-limiting example, the signal provided by temperature sensor 128 may facilitate determining and/or presenting an indication of the subject's core temperature, the subject's surface temperature, a temperature of an environment surrounding the subject, a change in a temperature, and/or other information associated with temperature. In some implementations, temperature sensor 128 may include one or more of a thermometer, a thermistor, a thermocouple, and/or other temperature sensor.

The blood pressure sensor 130 may be configured to provide a signal conveying information associated with a blood pressure of the subject during resuscitation. In some implementations, blood pressure sensor 130 may be configured to receive a signal conveying information associated with a blood pressure of the subject during resuscitation from an external source. For example, blood pressure sensor 130 may receive a signal from a sphygmomanometer or blood pressure sensor (not depicted) that is separate and distinct from apparatus 102. As such, blood pressure sensor 130 may be communicatively coupled with a sphygmomanometer or blood pressure sensor. In some implementations, blood pressure sensor 130 may include a microphone configured to record verbal announcements of the subject's blood pressure.

The oxygen saturation sensor 131 may be configured to provide a signal conveying information associated with an oxygen saturation of the subject's blood. By way of non-limiting example, the signal provided by oxygen saturation sensor 131 may facilitate determining and/or presenting an indication of a saturation of peripheral oxygen ($SpO_2$) associated with the subject.

The chest compression sensor 132 may be configured to provide a signal conveying information associated with chest compressions performed on the subject during resuscitation. By way of non-limiting example, the signal provided by chest compression sensor 132 may facilitate determining and/or presenting an indication of when a chest compression was performed on the subject, an amount of force applied to the subject by a chest compression, a displacement (depth) of the subject's chest cause by a chest compression, a rate of successive chest compressions, a pause in successive chest compressions, and/or other information associated with chest compressions performed on the subject. In some implementations, chest compression sensor 132 may include one or more accelerometers.

The cardioversion and/or defibrillation sensor 134 may be configured to provide a signal conveying information associated with cardioversion procedures and/or defibrillation procedures performed on the subject during resuscitation. By way of non-limiting example, the signal provided by cardioversion and/or defibrillation sensor 134 may facilitate determining and/or presenting an indication of when cardioversion procedures and/or defibrillation procedures were performed on the subject, an amount of energy associated with cardioversion procedures and/or defibrillation procedures performed on the subject, duration of the energy, synchronized versus unsynchronized, subject's response to a cardioversion procedure and/or a defibrillation procedure, and/or other information associated with cardioversion procedures and/or defibrillation procedures. The cardioversion and/or defibrillation sensor 134 may be communicatively coupled to a cardioversion and/or defibrillation device. The cardioversion and/or defibrillation sensor 134 may be configured to sense electrical currents applied to the subject. The cardioversion and/or defibrillation sensor 134 may include one or more of an ECG sensor, an accelerometer, a microphone, and/or other sensors.

The verbal communication sensor 136 may be configured to provide a signal conveying information associated with verbal communication among the members of the code blue team in an environment of the subject during resuscitation. The verbal communication sensor 136 may include one or more of a microphone, an acoustic-to-electric transducer, and/or other sensor configured to sense audio information.

The electronic storage 114 may be disposed within enclosure 108. The electronic storage 114 may be configured to store and provide access to information conveyed by the signals provided by sensor bank 112. According to some implementations, apparatus 102 may be assigned a unique serial number and a security code for accessing information stored by electronic storage 114. To access the stored information using a given personal computing device (e.g., personal computing device 104), the given personal computing device may be required to be paired with apparatus 102 via a Bluetooth link and/or other communicative connection, in accordance with some implementations.

In some implementations, a patient's identifiers may be recorded by virtue of a user verbally identifing the patient's name, a hospital ID number, a date of birth, and/or other patient information. In some implementations, apparatus 102 may be configured to wirelessly retrieve information including patient information from other electronic medical devices. The apparatus 102 may be configured to obtain patient information by scanning visual marks (e.g., barcode, QR code, and/or other visual marks), by imaging the patient's ID band, by a keypad, and/or by other techniques.

The processor(s) 116 may be disposed within enclosure 108. The processor(s) 116 may be configured to execute computer program instructions 138. The computer program instructions 138 may include a time stamping component 140 and/or other components. The time stamping component 140 may be configured to time stamp signals provided by sensor bank 112 and/or time stamp information conveyed by the signals provided by sensor bank 112. Such time stamps may facilitate chronological logging of code blue events.

The communications interface 118 may be disposed within enclosure 112. The communications interface 118 may be configured to communication with one or more other components of system 110 by wireless connections and/or wired connections. The communication interface 118 may be configured to transmit one or more of signals provided by sensor bank 112, information conveyed by the signals provided by sensor bank 112, information stored by electronic storage 114, information received from processor(s) 116, and/or other information. The communications interface 118 may be configured to receive information from one or more other components of system 100. According to some implementations, communications interface 118 may be compatible with one or more of a Bluetooth standard, a Wi-Fi standard, an ANT or ANT+ standard, a near-field standard, wireless data communication protocols, and/or other communications standards.

The personal computing platform 104 may include one or more of electronic storage 142, one or more processors 144, and/or other components. The processor(s) 144 may be configured to execute computer program instructions 146. The computer program instructions 146 may include one or more of a voice interpretation component 148, a code blue documentation component 150, and/or other components.

The voice interpretation component 148 may be configured to interpret one or more of a vital sign of the subject during resuscitation presented as a function of time, an action taken by a code blue team during the code blue scenario, and/or other information. The interpretation may be based on audio information from the environment surrounding the subject during resuscitation. The code blue team may include one or more healthcare providers, individual ones being assigned different roles and/or functions.

The code blue documentation component 150 may be configured to provide code blue documentation that conveys information related to the vital signs of the subject during resuscitation and the audio information from the environment surrounding the subject during resuscitation. The code blue documentation may include one or more of (1) one or more vital signs of the subject during resuscitation presented as a function of time, (2) one or more actions taken by a code blue team during the code blue scenario, the code blue team including one or more healthcare providers, (3) information based on the audio information from the environment of the subject during resuscitation presented as a function of time, and/or other information.

The one or more vital signs presented by the code blue documentation may include one or more of a heart rate of the subject during resuscitation, a cardiac rhythm of the subject during resuscitation, a respiration of the subject during resuscitation, chest movements of the subject with respiration during resuscitation, a temperature of the subject during resuscitation, a blood pressure of the subject during resuscitation, oxygen saturation (e.g., SpO2) of the subject during resuscitation, and/or other information associated with vital signs.

The one or more actions taken by the code blue team during the code blue scenario may include one or more of chest compressions performed on the subject during resuscitation, cardioversion procedures and/or defibrillation procedures performed on the subject during resuscitation, medications administered to the subject during resuscitation, endotracheal intubation, artificial respiration provided to the subject during resuscitation, vascular accesses (e.g., intravenous lines, intra-osseous lines, arterial lines, and/or other accesses), surgical procedures, laboratory test results associated with the subject, results from point-of-care devices associated with the subject, and/or other information associated with actions taken by the code blue team.

The information based on the audio information from the environment of the subject during resuscitation may include one or more of verbal commands issued by a leader of the code blue team, verbal responses to commands issued by a leader of the code blue team, chest compressions performed on the subject during resuscitation, cardioversion procedures and/or defibrillation procedures performed on the subject during resuscitation, verbal assessments of a status of the subject during resuscitation, verbal assessments of a vital sign of the subject during resuscitation, medications administered to the subject during resuscitation, endotracheal intubation and artificial respiration provided to the subject during resuscitation, vascular accesses (e.g., intravenous lines, intra-osseous lines, arterial lines, and/or other accesses), surgical procedures, laboratory test results associated with the subject, results from point-of-care devices associated with the subject, and/or other information associated with audio information from the environment surrounding the subject.

The code blue documentation may be provided and/or presented in various forms. In some implementations, the code blue documentation may be provided as an electronic document. By way of non-limiting example, the code blue documentation may be exported as a portable document file (PDF) or other electronic document format so that the code blue documentation can be printed for paper chart, or uploaded to an electronic medical record (EMR). The code blue documentation may be provided directly as an electronic medical record.

Figure 5:
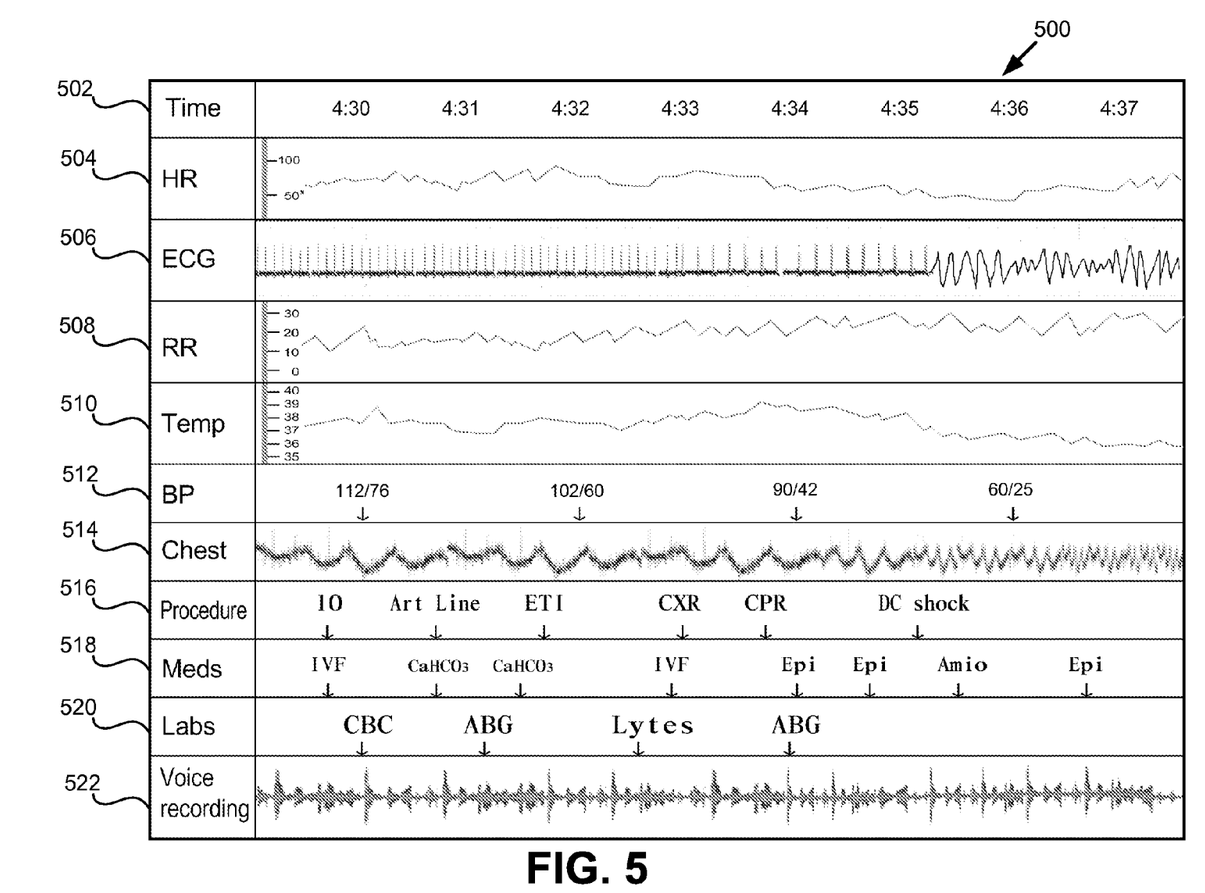
FIG. 5 illustrates a graphical user interface presenting code blue documentation, in accordance with one or more implementations.

In some implementations, the code blue documentation may be provided for presentation via portable computing platform 104. FIG. 5 illustrates a graphical user interface 500 presenting code blue documentation, in accordance with one or more implementations. The graphical user interface 500 may be presented by personal computing platform 104. The graphical user interface 500 may include one or more of a time field 502, a heart rate field 504, an ECG field 506, a respiratory rate field 508, a temperature field 510, a blood pressure field 512, an oxygen saturation field ($SpO_2$) (not depicted), a chest movement field 514, a procedure field 516, a medication field 518, a labs field 520, a voice recording field 522, and/or other fields. The fields of graphical user interface 500 presented in FIG. 5 are intended to be illustrative. In some implementations, graphical user interface 500 may include one or more additional fields not described, and/or without one or more of the fields discussed. Additionally, the order and/or arrangement in which the fields of graphical user interface 500 are illustrated in FIG. 5 are not intended to be limiting.

The fields of graphical user interface 500 may be configured to convey various information. The time field 502 may be configured to convey time information associated with a code blue scenario. The time information may include a time of day, a time since the code blue scenario was initiated, a time since apparatus 102 was adhered to the subject, and/or other time information associated with the code blue scenario. The heart rate field 504 may be configured to convey the subject's heart rate as a function of time and/or other information associated with the subject's heart rate. The ECG field 506 may be configured to convey the subject's electrocardiogram as a function of time, cardiac rhythm, identifying arrhythmias, and/or other information associated with the subject's ECG. The respiratory rate field 508 may be configured to convey the subject's respiratory rate as a function of time and/or other information associated with the subject's breathing. The temperature field 510 may be configured to convey the subject's temperature as a function of time and/or other information associated with the subject's temperature. The blood pressure field 512 may be configured to convey the subject's blood pressure as a function of time and/or other information associated with the subject's blood pressure. The chest movement field 514 may be configured to convey the subject's chest movements as a function of time and/or other information associated with the subject's chest movements. The procedure field 516 may be configured to convey indications of performed procedures as a function of time, the nature or type of individual procedures, and/or other information associated with procedures performed on the subject. The medication field 518 may be configured to convey indications of provided medications as a function of time, the type and/or dosage of individual medications, and/or other information associate with medications provided to the subject during the code blue scenario. The labs field 520 may be configured to convey indications of performed labs (e.g., assays) as a function of time, the nature or type of individual labs, and/or other information related to labs associated with the code blue scenario. The voice recording field 522 may be configured to convey audio information recorded in the environment surrounding the subject during the code blue scenario. The audio information may be transcribed into text. The graphical user interface 500 may be configured to facilitate audible playback of audio information. In some implementations, graphical user interface 500 may be configured to facilitate zooming in and out of a graphical representation of audio information (e.g., zoom in to view one second of audio information, zoom out to fit the size of a screen, and/or other zoom configurations). In some implementations, graphical user interface 500 may be configured to convey a detailed analysis of chest compressions (e.g., rate, depth, pauses, and intervals). Onscreen calipers may be provided to measure time intervals between events and measure time intervals for one or more quality of care indicators.

Turning back to FIG. 1, in some implementations, apparatus 102, personal computing platform 104, server 106, and/or external resources 152 may be operatively linked via one or more electronic communication links. For example, such electronic communication links may be established, at least in part, via a network or connection such as the Internet, Wi-Fi, Bluetooth, and/or other networks or connections. It will be appreciated that this is not intended to be limiting, and that the scope of this disclosure includes implementations in which apparatus 102, personal computing platform 104, server 106, and/or external resources 152 may be operatively linked via some other communication media.

By way of non-limiting example, a given personal computing platform 104 may include one or more of a desktop computer, a laptop computer, a handheld computer, a tablet computing platform, a NetBook, a Smartphone, and/or other computing platforms.

Server 106 may include electronic storage, one or more processors, and/or other components. Server 106 may be configured to execute computer program instructions 138, computer program instructions 146, and/or other instructions. Server 106 may include communication lines, or ports to enable the exchange of information with a network and/or other computing platforms. Illustration of server 106 in FIG. 1 is not intended to be limiting. Server 106 may include a plurality of hardware, software, and/or firmware components operating together to provide the functionality attributed herein to server 106. For example, server 106 may be implemented by a cloud of computing platforms operating together as server 106.

External resources 152 may include sources of information, hosts and/or providers of medical information (e.g., EMR) outside of system 100, external entities participating with system 100, and/or other resources. In some implementations, some or all of the functionality attributed herein to external resources 152 may be provided by resources included in system 100.

Electronic storage 114 and/or 142 may comprise non-transitory storage media that electronically stores information. The electronic storage media of electronic storage 114 and/or 142 may include one or both of system storage that is provided integrally (i.e., substantially non-removable) with a device (e.g., apparatus 102 or personal computing platform 104) and/or removable storage that is removably connectable to the device (e.g., apparatus 102 or personal computing platform 104), for example, a port (e.g., a USB port, a firewire port, etc.) or a drive (e.g., a disk drive, etc.). Electronic storage 114 and/or 142 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 114 and/or 142 may include one or more virtual storage resources (e.g., cloud storage, a virtual private network, and/or other virtual storage resources). Electronic storage 114 and/or 142 may store software algorithms, information determined by a processor (e.g., processor(s) 116 and/or processor(s) 144), information received from server 106, information received from personal computing platforms 104, information received from apparatus 102, information received from external resources 152, and/or other information that system 100 to function as described herein.

Processor(s) 116 may be configured to provide information processing capabilities in apparatus 102. Processor(s) 144 may be configured to provide information processing capabilities in personal computing platform 104. As such, processor(s) 116 and/or 144 may include one or more of a digital processor, an analog processor, a digital circuit designed to process information, an analog circuit designed to process information, a state machine, and/or other mechanisms for electronically processing information. Although processor(s) 116 and 144 are shown in FIG. 1 as single entities, this is for illustrative purposes only. In some implementations, processor processor(s) 116 and/or 114 may include a plurality of processing units. These processing units may be physically located within the same device, or processor(s) 116 and/or 114 may represent processing functionality of a plurality of devices operating in coordination. The processor(s) 116 and/or 114 may be configured to execute computer program instructions (e.g., computer program instructions 138 and/or 146) by software; hardware; firmware; some combination of software, hardware, and/or firmware; and/or other mechanisms for configuring processing capabilities on processor(s) 116 and/or 114. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although computer program instruction components 140, 148, and 150 are illustrated in FIG. 1 as being implemented within a single processing unit, in implementations in which processor(s) 116 and/or 114 includes multiple processing units, one or more of components 140, 148, and/or 150 may be implemented remotely from the other components. The description of the functionality provided by the different components 140, 148, and/or 150 described herein is for illustrative purposes, and is not intended to be limiting, as any of components 140, 148, and/or 150 may provide more or less functionality than is described. For example, one or more of components 140, 148, and/or 150 may be eliminated, and some or all of its functionality may be provided by other ones of components 140, 148, and/or 150. As another example, processor(s) 116 and/or 114 may be configured to execute one or more additional components that may perform some or all of the functionality attributed below to one of components 140, 148, and/or 150.

Figure 6:
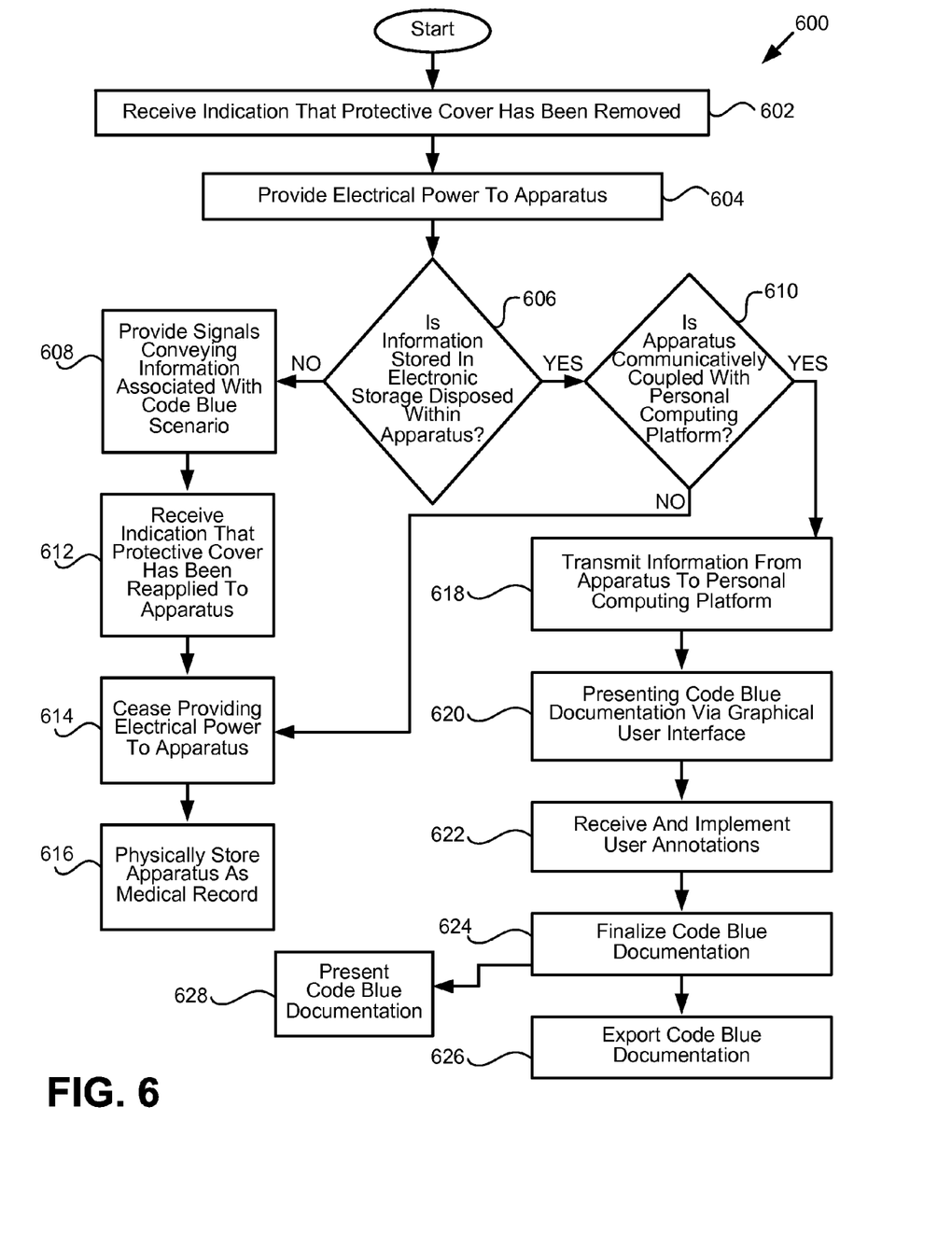
FIG. 6 illustrates a method for documenting code blue scenarios, in accordance with one or more implementations.

FIG. 6 illustrates a method 600 for documenting code blue scenarios, in accordance with one or more implementations. The operations of method 600 presented below are intended to be illustrative. In some implementations, method 600 may be accomplished with one or more additional operations not described, and/or without one or more of the operations discussed. Additionally, the order in which the operations of method 600 are illustrated in FIG. 6 and described below is not intended to be limiting.

In some implementations, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, an indication may be received conveying that a protective cover has been removed from an apparatus (e.g., apparatus 102) configured to be adhered to the chest of a subject when the code blue scenario begins. In some implementations, operation 602 may be performed by processor(s) 116.

At an operation 604, electrical power may be provided to the apparatus. Operation 604 may be performed by power supply 110, according to some implementations. According to various implementations, the electrical power may be provided responsive to the protective cover being removed and/or the apparatus being applied to the subject.

At an operation 606, electronic storage (e.g., electronic storage 114) disposed within the apparatus may be queried to determine whether information associated with a code blue scenario is stored in the electronic storage. In some implementations, operation 606 may be performed by processor(s) 116. If the determination in operation 606 is positive, method 600 may proceed to an operation 608. If the determination in operation 606 is negative, method 600 may proceed to an operation 610.

At operation 608, a sensor bank (e.g., sensor bank 112) disposed in the apparatus begins providing signals conveying information associated with the code blue scenario, which form a basis for code blue documentation.

At an operation 612, an indication may be received conveying that the protective cover has been reapplied to the apparatus. In some implementations, operation 612 may be performed by processor(s) 116.

At an operation 614, electrical power ceases to be provided to the apparatus. According to various implementations, the electrical power may cease to be provided responsive to the protective cover being reapplied to the apparatus and/or the apparatus being placed into a container.

At an operation 616, the apparatus may be physically stored as a medical record.

Looking back to operation 610, a determination may be made as to whether the apparatus is communicatively coupled with a personal computing platform (e.g., personal computing platform 104). In some implementations, operation 610 may be performed by processor(s) 116 in conjunction with communications interface 118. If the determination in operation 610 is negative, method 600 may proceed to operation 614. If the determination in operation in operation 610 is positive, method 600 may proceed to operation 618.

At operation 618, information associated with the signals provided by the sensor bank may be transmitted from the apparatus to the personal computing platform. In some implementations, operation 618 may be performed by processor(s) 116 in conjunction with communications interface 118.

At an operation 620, the personal computing platform may display a graphical user interface (e.g., graphical user interface 500) presenting code blue documentation. Operation 620 may be performed by processor(s) 144, according to some implementations.

At an operation 622, user annotations may be received by the personal computing platform and implemented in the code blue documentation. Operation 622 may be performed by processor(s) 144, according to some implementations.

At an operation 624, the code blue documentation may be finalized based on one or both of the information received from the apparatus and/or user annotations. Operation 624 may be performed by processor(s) 144, according to some implementations.

At an operation 626, the code blue documentation may be exported in an electronic document format (e.g., PDF). Operation 626 may be performed by processor(s) 144, according to some implementations.

At an operation 628, the code blue documentation may be presented for review of quality, educational purposes, and/or other purposes. Operation 628 may be performed by processor(s) 144, according to some implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. An apparatus configured for documenting a code blue scenario when adhered to the chest of a subject undergoing resuscitation, the apparatus comprising:
   an enclosure configured to withstand compressive forces applied to the subject's chest from chest compressions during resuscitation of the subject such that components disposed within the enclosure are protected from mechanical damage;
a sensor bank at least partially disposed within the enclosure, the sensor bank being configured to provide signals conveying information associated with a code blue scenario, the information including vital signs of the subject during resuscitation and audio information from an environment surrounding the subject during resuscitation, the sensor bank including:
a heart rate sensor configured to provide a signal conveying information associated with a heart rate of the subject during resuscitation;
a chest movement sensor configured to provide a signal conveying information associated with chest movements caused by artificial respiration provided to the subject during resuscitation;
a chest compression sensor configured to provide a signal conveying information associated with chest compressions performed on the subject during resuscitation; and
a verbal communication sensor configured to provide a signal conveying information associated with verbal communication in an environment of the subject during resuscitation; and
one or more hardware processors at least partially disposed within the enclosure, the one or more hardware processors being configured by machine-readable instructions to:
receive a signal from the heart rate sensor conveying information associated with the heart rate of the subject during resuscitation;
receive a signal from the chest movement sensor conveying information associated with chest movements caused by artificial respiration provided to the subject during resuscitation;
receive a signal from the chest compression sensor configured to provide a signal conveying information associated with chest compressions performed on the subject during resuscitation;
receive a signal from the verbal communication sensor configured to provide a signal conveying information associated with verbal communication in an environment of the subject during resuscitation; and
provide information from the signals received from the sensors to populate an electronic code blue sheet, the electronic code blue sheet being a user interface configured to automatically display recorded code blue events chronologically with time stamps, provide zoomable views of vital signs, and facilitate playback of the verbal communication.

2. The apparatus of claim 1, wherein the information conveyed by signals provided by the sensor bank further includes information associated with chest movements of the subject during resuscitation.

3. The apparatus of claim 1, wherein the enclosure is further configured to removably adhere to the subject's chest.

4. The apparatus of claim 1, further comprising a power supply disposed within the enclosure, the power supply being configured to provide electrical power to one or more components of the apparatus.

5. The apparatus of claim 4, wherein the power supply is configured to provide electrical power to one or more components of the apparatus responsive to one or both of the apparatus being removably adhered to a subject's chest or an adhesive cover being removed from the enclosure.

6. The apparatus of claim 1, wherein the sensor bank includes one or more of:
a cardiac rhythm sensor configured to provide a signal conveying information associated with a cardiac rhythm of the subject during resuscitation;
a respiration sensor configured to provide a signal conveying information associated with a respiration of the subject during resuscitation;
a temperature sensor configured to provide a signal conveying information associated with a temperature of the subject during resuscitation;
a blood pressure sensor configured to provide a signal conveying information associated with a blood pressure of the subject during resuscitation;
an oxygen saturation sensor configured to provide a signal conveying information associated with an oxygen saturation of the subject during resuscitation; or
a cardioversion and/or defibrillation sensor configured to provide a signal conveying information associated with cardioversion procedures and/or defibrillation procedures performed on the subject during resuscitation.

7. The apparatus of claim 1, wherein the audio information from the environment includes voice commands issued during resuscitation of the subject.

8. The apparatus of claim 1, wherein the audio information from the environment includes a vocal indication of a vital sign of the subject during resuscitation.

9. The apparatus of claim 1, further comprising an electronic storage disposed within the enclosure, the electronic storage being configured to store and provide access to information conveyed by the signals provided by the sensor bank.

10. The apparatus of claim 1, further comprising one or more processors disposed within the enclosure, the one or more processors being configured to execute computer program instructions, the computer program instructions including a time stamping component, the time stamping component being configured to:
time stamp signals provided by the sensor bank; or
time stamp information conveyed by the signals provided by the sensor bank.

11. The apparatus of claim 1, further comprising a communications interface disposed within the enclosure, the communications interface being configured to transmit one or both of:
signals provided by the sensor bank; or
information conveyed by the signals provided by the sensor bank.

12. A system configured for documenting code blue scenarios, the system comprising:
one or more physical processors configured to receive information from an apparatus configured for documenting a code blue scenario when adhered to the chest of a subject undergoing resuscitation by sensing and transmitting information associated with the code blue scenario, the information including vital signs of the subject during resuscitation and audio information from an environment of the subject during resuscitation, the one or more physical processors being disposed at a location other than the apparatus, the one or more physical processors being further configured to execute computer program instructions, the computer program instructions comprising:
a code blue documentation component configured to provide code blue documentation that conveys information related to the vital signs of the subject during resuscitation and the audio information from the environment of the subject during resuscitation, wherein the apparatus comprises:
- an enclosure configured to withstand compressive forces applied to the subject's chest from chest compressions during resuscitation of the subject such that components disposed within the enclosure are protected from mechanical damage;
- a sensor bank at least partially disposed within the enclosure, the sensor bank being configured to provide signals conveying information associated with a code blue scenario, the information including vital signs of the subject during resuscitation and audio information from an environment surrounding the subject during resuscitation, the sensor bank including:
  - a heart rate sensor configured to provide a signal conveying information associated with a heart rate of the subject during resuscitation;
  - a chest movement sensor configured to provide a signal conveying information associated with chest movements caused by artificial respiration provided to the subject during resuscitation;
  - a chest compression sensor configured to provide a signal conveying information associated with chest compressions performed on the subject during resuscitation; and
  - a verbal communication sensor configured to provide a signal conveying information associated with verbal communication in an environment of the subject during resuscitation; and
- one or more hardware processors at least partially disposed within the enclosure, the one or more hardware processors being configured by machiner-readable instructions to:
  - receive a signal from the heart rate sensor conveying information associated with the heart rate of the subject during resuscitation;
  - receive a signal from the chest movement sensor conveying information associated with chest movements caused by artificial respiration provided to the subject during resuscitation;
  - receive a signal from the chest compression sensor configured to provide a signal conveying information associated with chest compressions performed on the subject during resuscitation;
  - receive a signal from the verbal communication sensor configured to provide a signal conveying information associated with verbal communication in an environment of the subject during resuscitation; and
  - provide information from the signals received from the sensors to populate an electronic code blue sheet, the electronic code blue sheet being a user interface configured to automatically display recorded code blue events chronologically with time stamps, provide zoomable views of vital signs, and facilitate playback of the verbal communication.

13. The system of claim 12, wherein the apparatus is further configured to be removably adhered to a subject's chest.

14. The system of claim 12, wherein a given one of the one or more processors are disposed within a personal computing platform that is physically separate and distinct from the apparatus.

15. The system of claim 12, wherein a given one of the one or more processors are disposed within a server that is remotely located from the apparatus.

16. The system of claim 12, wherein the code blue documentation is provided for presentation via a personal computing platform.

17. The system of claim 12, wherein the code blue documentation is provided as an electronic document.

18. The system of claim 12, wherein the code blue documentation is provided as an electronic medical record.

19. The system of claim 12, wherein the code blue documentation is provided as a printed record for a conventional paper record.

20. The system of claim 12, wherein the code blue documentation includes one or more of:
- one or more vital signs of the subject during resuscitation presented as a function of time;
- one or more actions taken by a code blue team during the code blue scenario, the code blue team including one or more healthcare providers; or
- information based on the audio information from the environment of the subject during resuscitation presented as a function of time.

21. The system of claim 20, wherein the one or more vital signs presented by the code blue documentation includes one or more of a heart rate of the subject during resuscitation, a cardiac rhythm of the subject during resuscitation, a respiration of the subject during resuscitation, chest movements performed by the subject during resuscitation, a temperature of the subject during resuscitation, a blood pressure of the subject during resuscitation, or an oxygen saturation of the subject during resuscitation.

22. The system of claim 20, wherein the one or more actions taken by the code blue team during the code blue scenario includes one or more of chest compressions performed on the subject during resuscitation, cardioversion procedures and/or defibrillation procedures performed on the subject during resuscitation, medications administered to the subject during resuscitation, endotracheal intubation and artificial respiration provided to the subject during resuscitation, vascular access procedures provided to the subject during resuscitation, surgical procedures provided to the subject during resuscitation, laboratory test results associated with the subject obtained during resuscitation, or results from point-of-care devices associated with the subject obtained during resuscitation.

23. The system of claim 20, wherein the information based on the audio information from the environment of the subject during resuscitation includes one or more of verbal commands issued by a leader of the code blue team, verbal responses to commands issued by a leader of the code blue team, chest compressions performed on the subject during resuscitation, cardioversion procedures and/or defibrillation procedures performed on the subject during resuscitation, verbal assessments of a status of the subject during resuscitation, verbal assessments of a vital sign of the subject during resuscitation, medications administered to the subject during resuscitation, endotracheal intubation and artificial respiration provided to the subject during resuscitation, vascular access procedures provided to the subject during resuscitation, surgical procedures provided to the subject during resuscitation, laboratory test results associated with the subject obtained during resuscitation, or results from point-of-care devices associated with the subject obtained during resuscitation.

24. The system of claim 12, wherein the computer program instructions further comprise a voice interpretation component configured to interpret one or both of a vital sign of the subject during resuscitation presented as a function of time or an action taken by a code blue team during the code blue scenario, the interpretation being based on audio information from the environment surrounding the subject during resuscitation, the code blue team including one or more healthcare providers.

25. A method for documenting code blue scenarios, the method comprising:

utilizing an apparatus configured for documenting a code blue scenario when adhered to the chest of a subject undergoing resuscitation, the apparatus comprising:

an enclosure configured to withstand compressive forces applied to the subject's chest from chest compressions during resuscitation of the subject such that components disposed within the enclosure are protected from mechanical damage;

a sensor bank at least partially disposed within the enclosure, the sensor bank being configured to provide signals conveying information associated with a code blue scenario, the information including vital signs of the subject during resuscitation and audio information from an environment surrounding the subject during resuscitation, the sensor bank including:

a heart rate sensor configured to provide a signal conveying information associated with a heart rate of the subject during resuscitation;

a chest movement sensor configured to provide a signal conveying information associated with chest movements caused by artificial respiration provided to the subject during resuscitation;

a chest compression sensor configured to provide a signal conveying information associated with chest compressions performed on the subject during resuscitation; and a verbal communication sensor configured to provide a signal conveying information associated with verbal communication in an environment of the subject during resuscitation; and one or more hardware processors at least partially disposed within the enclosure, the one or more hardware processors being configured by machine-readable instructions to:

receive a signal from the heart rate sensor conveying information associated with the heart rate of the subject during resuscitation;

receive a signal from the chest movement sensor conveying information associated with chest movements caused by artificial respiration provided to the subject during resuscitation;

receive a signal from the chest compression sensor configured to provide a signal conveying information associated with chest compressions performed on the subject during resuscitation;

receive a signal from the verbal communication sensor configured to provide a signal conveying information associated with verbal communication in an environment of the subject during resuscitation; and provide information from the signals received from the sensors to populate an electronic code blue sheet, the electronic code blue sheet being a user interface configured to automatically display recorded code blue events chronologically with time stamps, provide zoomable views of vital signs, and facilitate playback of the verbal communication.

* * * * *